United States Patent [19]

Penco et al.

[11] 4,169,142
[45] Sep. 25, 1979

[54] DISACCHARIDE ANALOGS OF ANTITUMOR ANTHRACYCLINES, PROCESS FOR THEIR PREPARATION AND USE THEREOF

[75] Inventors: Sergio Penco; Giuliano Franchi; Federico Arcamone, all of Milan, Italy

[73] Assignee: Societa' Farmaceutici Italia S.p.A., Milan, Italy

[21] Appl. No.: 851,165

[22] Filed: Nov. 14, 1977

[30] Foreign Application Priority Data

Nov. 17, 1976 [GB] United Kingdom ............... 47835/76

[51] Int. Cl.$^2$ ..................... A61K 31/70; C07G 11/00
[52] U.S. Cl. ................................. 424/180; 536/17 A
[58] Field of Search ........................... 536/17; 424/180

[56] References Cited

U.S. PATENT DOCUMENTS 3,686,163  8/1972  Arcamone et al. ............... 536/17 A

FOREIGN PATENT DOCUMENTS 2548087  6/1976  Fed. Rep. of Germany ........ 536/17 A

*Primary Examiner*—Ethel G. Love
*Attorney, Agent, or Firm*—Hubbell, Cohen, Stiefel & Gross

[57] ABSTRACT

Anthracycline disaccharides having antitumor activity are prepared by condensing N-trifluoroacetyldaunomycin with a 1-halosugar in the presence of a silver salt such as AgSO$_3$CF$_3$ as catalyst to form a protected diglycoside which upon mild alkaline hydrolysis yields the novel disaccharides.

7 Claims, No Drawings

DISACCHARIDE ANALOGS OF ANTITUMOR ANTHRACYCLINES, PROCESS FOR THEIR PREPARATION AND USE THEREOF

The invention described herein was made in the course of work under a grant from the U.S. Department of Health, Education and Welfare.

BACKGROUND OF THE INVENTION

1. Field of the Invention

The invention relates to anthracycline antibiotics, processes for preparing them, novel intermediates used in the preparation thereof and methods of using them in the treatment of certain tumors.

2. The Prior Art

U.S. Pat. No. 3,686,163, owned by the unrecorded assignee hereof, discloses C-4'-daunosaminyldaunomycin as a biologically active metabolite of *Streptomyces peucetius var. carneus*. This compound, however, has never been made before by chemical synthesis.

SUMMARY OF THE INVENTION

The present invention is concerned with a group of new disaccharide derivatives of anthracyclines of the formula I. The compounds of formula I are endowed with considerable antimitotic activity in different tumor systems and are therefore useful anticancer agents. More precisely the compounds of the invention are characterized by the following patterns of substitution:

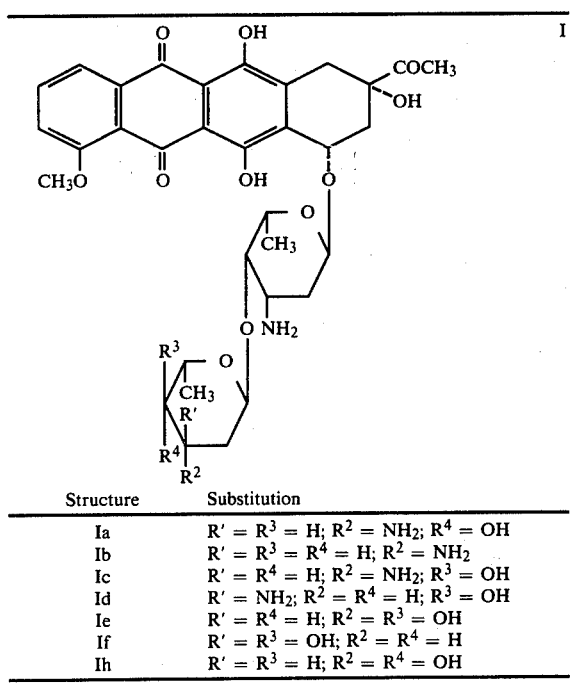

| Structure | Substitution |
|-----------|--------------|
| Ia | $R' = R^3 = H; R^2 = NH_2; R^4 = OH$ |
| Ib | $R' = R^3 = R^4 = H; R^2 = NH_2$ |
| Ic | $R' = R^4 = H; R^2 = NH_2; R^3 = OH$ |
| Id | $R' = NH_2; R^2 = R^4 = H; R^3 = OH$ |
| Ie | $R' = R^4 = H; R^2 = R^3 = OH$ |
| If | $R' = R^3 = OH; R^2 = R^4 = H$ |
| Ih | $R' = R^3 = H; R^2 = R^4 = OH$ |

Each of compounds Ib, Ic, Id, Ie If and Ih are novel compounds, while compound Ia, as noted above, has been described in U.S. Pat. No. 3,686,163.

Thus, in one aspect, the invention provides, as a new class of compounds, the compounds according to formula I except for compound Ia.

In another aspect, the invention provides a process for preparing the compounds of formula I, including the known compound Ia, which has not heretofore been made synthetically.

As will appear below, the process for making compounds Ia to Ih involves the use of certain novel intermediates of the formula IV. Thus, in yet another aspect, the invention provides these novel intermediates IV.

Finally, in still another aspect, the invention provides a method of treating certain mammalian tumors using the compounds of formula I.

The process for preparing compounds Ia–Ih is performed according to the following scheme:

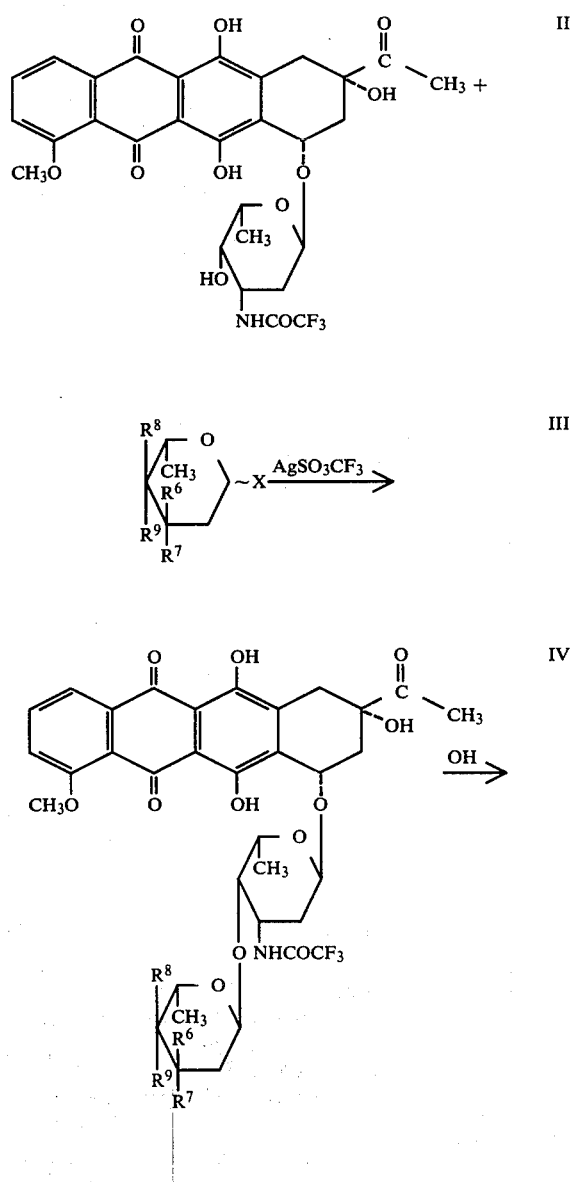

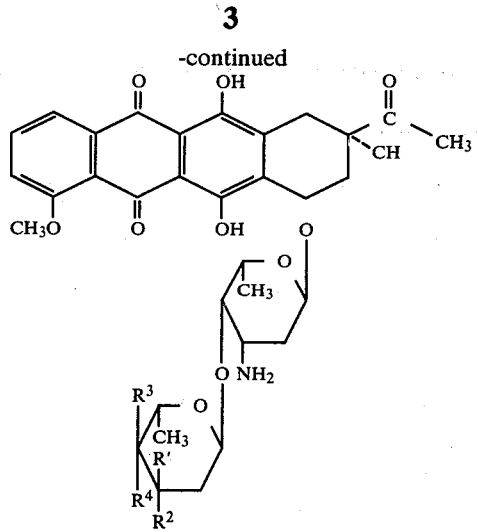

The 1-halosugars (X=Br, Cl) of the formula III wherein X is Br or Cl, are characterized by the following substitution patterns (pNBz=p-nitrobenzoyl):

| Structure | Substitution |
|---|---|
| IIIa | $R^6 = R^8 = H; R^7 = NHCOCF_3; R^9 = OCOCF_3$ |
| IIIb | $R^6 = R^8 = R^9 = H; R^7 = NHCOCF_3$ |
| IIIc | $R^6 = R^9 = H; R^7 = NHCOCF_3; R^8 = OCOCF_3$ |
| IIId | $R^6 = NHCOCF_3; R^7 = R^9 = H; R^8 = OpNBz$ |
| IIIe | $R^6 = R^9 = H; R^7 = R^8 = OpNBz$ |
| IIIf | $R^6 = R^8 = OpNBz; R^7 = R^9 = H$ |
| IIIh | $R^6 = R^8 = H; R^7 = R^9 = OpNBz$ |

More particularly, the starting materials for the new antitumor glycosides are N-trifluoroacetyldaunomycin II and the 1-halosugar (formulae IIIa–IIIh). The process for the synthesis of the glycoside linkage comprises treating compound II with the appropriate protected 1-halosugar, in a suitable organic solvent such as chloroform or methylene chloride in the presence of a soluble silver salt as a catalyst. This reaction can be exemplified by using 1-chloro-N,O-trifluoroacetyl daunosamine (IIIa), as a representative of the halosugar reagents. The coupling reaction leads to the protected glycoside IV ($R^6=R^8=H$; $R^7=NHCOCF_3$; $R^9=OH$) from which, by mild alkaline treatment in order to remove the protective N-trifluoroacetyl group, compound Ia, isolated as the hydrochloride, is obtained. The new compounds Ib–Ih, as well as the known compound Ia, display antimitotic activity and are useful therapeutic agents for the treatment of tumor diseases in mammals.

DESCRIPTION OF THE PREFERRED EMBODIMENTS

The following preparative examples are given to illustrate the process according to the invention which is used for making the novel compounds of the invention (as well as the heretofore known compound Ia). All parts given are by weight, unless otherwise indicated.

EXAMPLE 1

C-4'-Daunosaminyldaunomycin Ia

A solution of 6.48 g. of N-trifluoroacetyldaunomycin in 420 ml. of anhydrous methylene chloride containing 4.5 g. of 1-chloro-N,O-trifluoroacetyl-daunosamine, is treated in the presence of 50 g. of molecular sieve (4 Å, Merck) with 3.25 g. of AgSO₃CF₃, added in four portions over a period of 20 minutes with vigorous stirring, and 1.38 ml. of 2,6-lutidine. After two hours at room temperature, a sample of the reaction mixture, when subjected to thin layer chromatography (TLC) on Kieselgel F₂₅₄ (Merck) using the solvent system: CHCl₃/(CH₃)₂CO:4:1 v/v showed a new, and less polar product in about 30% yield. A saturated aqueous solution of NaHCO₃ was then added to the reaction mixture with vigorous stirring. After ten hours, the organic phase, after being separated, was evaporated under vacuum to form a residue which was dissolved in 100 ml. of acetone and treated with 0.1 N NaOh at 0° C. After 30 minutes at 0° C., the solution was adjusted to pH 8.5 with 0.1 N HCl and extracted with chloroform until the extracts were colorless. The organic extracts were combined, dried over Na₂SO₄ and evaporated to dryness under vacuum. The resulting residue was purified by chromatography on a column of silicic acid using as the eluent, the solvent system: CHCl₃—CH₃OH—H₂O (14:6:1 v/v). The fractions containing daunomycin and other by products were eliminated, while the fractions containing the product Ia were collected. The pH was adjusted to 4.5 and water was added. The red aqueous phase was separated, adjusted to pH 8.5 and extracted with chloroform. All of the red product was extracted into the organic phase, which was separated and then extracted with water at pH 4.8. Again, the entire product was extracted into the aqueous phase, which was evaporated under vacuum in the presence of an excess of butyl alcohol. When the water was completely removed, the alcoholic solution was evaporated to a small volume (10 ml.) and the precipitate which separated, was collected and washed with ether to obtain 0.5 g. of pure Ia m.p. 161° (dec.) TLC on silica gel plate buffered at pH 7 with 0.067 M phosphate; solvent system CHCl₃—CH₃OH—H₂O (14:6:1 v/v); Rf=0.25.

Elemental analysis for: $C_{33}H_{42}Cl_2N_2O_{12}$; Calculated % H 5.81; C 54.31; N 3.84; Cl 9.72; Found % 5.59; 53.77; 3.91; 9.24.

EXAMPLE 2

C-4'-(4''-epi)-daunosaminyldaunomycin

A solution of 2.18 g. of N-trifluoroacetyldaunomycin in 140 ml. of anhydrous methylene chloride containing 1.5 g of 1-chloro-N,O-trifluoroacetyl-4-epi-daunosamine (IIIc), was treated in the presence of 18 g. of molecular sieve (4 Å, Merck) with 1.09 g. of AgSO₃CF₃, added in four portions over 20 minutes with vigorous stirring and 0.46 ml. of 2,6-lutidine. Following the procedure described in Example 1, there was obtained 0.09 g. of pure Ic, m.p. 176° (dec.): TLC on silica gel plate F₂₅₄ (Merck) solvent system CHCl₃—CH₃OH—H₂O (14:6:1 v/v); Rf=0.2.

Elemental analysis for: $C_{33}H_{42}Cl_2N_2O_{12}$; Calculated % H 5.81; C 54.31; N 3.84; Found % 5.90; 54.21; 3.67.

EXAMPLE 3

C-4'-(2,6-dideoxy-α-L-arabinohexopyranosyl)daunomycin Ie

A solution of 14.50 g. of N-trifluoroacetyldaunomycin in 700 ml. of anhydrous methylene chloride containing 13 g. of 1-chloro-2,6-dideoxy-3,4-O-nitrobenzoyl-arabinohexopyranose (III e), was treated in the presence of 140 g. of molecular sieve (4 Å, Merck), with 7.28 g. of AgSO₃CF₃, added in four portions over 30 minutes with various stirring, and 3.08 ml. of 2,6-lutidine. Following the procedure described in Example 1, there were obtained 1.25 g. of pure Ie, m.p. 152°–157° (dec.): TLC on silica gel plate $F_{254}$ (Merck), solvent system $CH_2Cl_2$—$CH_3OH$—$H_2O$ (10:2:0.2 v/v); Rf=0.4.

Elemental analysis for: $C_{33}H_{40}ClNO_{13}$; Calculated % H 5.82; C 57.09; N 2.02; Cl 5.11; Found % 5.43; 57.13; 1.87; 5.00.

The other new compounds embraced by formula I can, of course, be made by the same procedure by simply using a different halo sugar III.

BIOLOGICAL ACTIVITY

The products according to the invention were tested under the auspices of NCI—National Institute of Health, Bethesda, Md., USA against Lymphocytic Leukemia $P_{388}$ according to the procedure described in Cancer Chemotherapy Reports, Part 3, volumn 3, page 9 (1972).

The data in the following tables illustrate the antitumor activity of some of the new anthracycline disaccharides of the invention.

The new compounds Ic and Ie (Table 1) were compared to daunomycin by treatment of $CDF_1$ female mice infected with tumor cells. The i.p. injections were made on days 5, 9 and 13 (4 day interval between each injection) starting from the fifth day after tumor transplantation in the mice. The activity of compound Ia was tested by i.p. treatment on days 1 to 9 in infected $CDF_1$ male mice. The median survival time expressed as percent of controls (T/C %) are reported in Table 2.

TABLE 1

| Compound | Schedule of Treatment in days (i.p) | Dose mg./kg. | T/C % |
|---|---|---|---|
| C-4-(4"-epi)-daunosaminyl-daunomycin . HCl Ic | | 50.0 | 112 |
| | | 25.0 | 121 |
| | 5, 9, 13 | 12.5 | 103 |
| | | 6.25 | 103 |
| | | 3.13 | 112 |
| C-4'-(2,6-dideoxy-α-L-arabinohexopyranosyl)-daunomycin . HCl Ie | | 50.0 | 135 |
| | | 25.0 | 117 |
| | | 12.5 | 119 |
| | 5, 9, 13 | 6.25 | 119 |
| | | 3.13 | 108 |
| Daunomycin . HCl | | 32.0 | 91 |
| | | 16.0 | 134 |
| | 5, 9, 13 | 8.0 | 119 |
| | | 4.0 | 128 |

Table 2

| Compound | Schedule of treatment in days (i.p.) | Dose mg./kg. | T/C % |
|---|---|---|---|
| C-4'-daunosaminyl-daunomycin.HCl Ia | | 25.0 | 59 |
| | | 12.5 | 86 |
| | | 6.25 | 146 |
| | 1 to 9 | 3.13 | 196 |
| | | 1.56 | 149 |
| Daunomycin.HCl | | 4.0 | 87 |
| | | 2.0 | 112 |
| | 1 to 9 | 1.0 | 166 |
| | | 0.5 | 158 |
| | | 0.25 | 149 |

Variations and modifications can, of course, be made without departing from the spirit and scope of the invention.

Having thus described our invention what we desire to secure by Letters Patent and hereby claim is:

1. A compound of the formula:

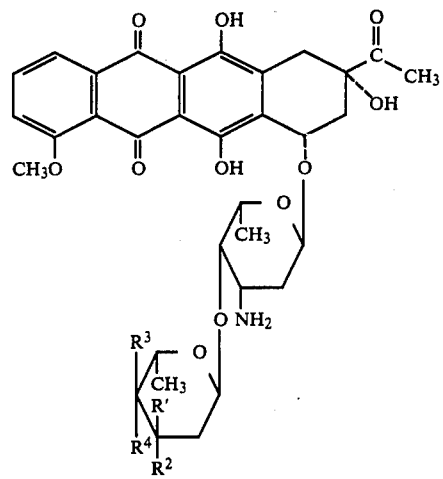

wherein R' and $R_2$ are H, OH or $NH_2$ and $R_3$ and $R_4$ are H or OH, provided that when $R_2$ is $NH_2$, $R_4$ is H, and the hydrochlorides thereof.

2. A compound according to claim 1, which is C-4'-(4"-epi)daunosaminyldaunomycin and the hydrochloride thereof.

3. A compound according to claim 1, which is C-4'-(2,6-dideoxy-α-L-arabinohexopyranosyl)daunomycin and the hydrochloride thereof.

4. A compound of the formula:

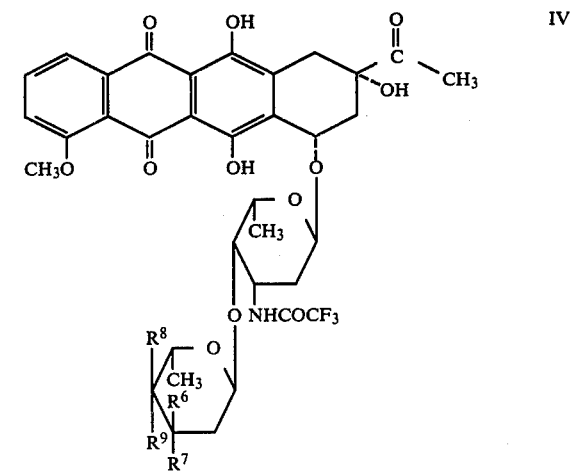

wherein $R_6$ and $R_7$ are H, $NHCOCF_3$ or —O—p-nitrobenzoyl and $R_8$ and $R_9$ are H, $OCOCF_3$ or p-nitrobenzoyl.

5. A composition for inhibiting the growth of lymphocytic leukemia $P_{388}$ comprising a compound according to claim 1 in an amount sufficient to inhibit the growth thereof and a carrier therefor.

6. A method of inhibiting the growth of lymphocytic leukemia $P_{388}$ which comprises administering to a host afflicted therewith, a compound according to claim 1 in an amount sufficient in inhibit the growth thereof.

7. A method according to claim 6, wherein said compound is administered intraperitoneally.